US00PP36972P2

(12) United States Plant Patent
van Eijk

(10) Patent No.: US PP36,972 P2
(45) Date of Patent: Sep. 16, 2025

(54) ***ZANTEDESCHIA* PLANT NAMED 'EYD21WC102'**

(50) Latin Name: *Zantedeschia aethiopica*
Varietal Denomination: EYD21WC102

(71) Applicant: EIJCO B.V., Nootdorp (NL)

(72) Inventor: Cornelis H. A. van Eijk, Nootdorp (NL)

(73) Assignee: EIJCO B.V., Nootdorp (NL)

( * ) Notice: Subject to any disclaimer, the term of this patent is extended or adjusted under 35 U.S.C. 154(b) by 0 days.

(21) Appl. No.: 19/004,285

(22) Filed: Dec. 28, 2024

(51) Int. Cl.
*A01H 5/02* (2018.01)
*A01H 6/10* (2018.01)

(52) U.S. Cl.
USPC ..... Plt./490
CPC ..... *A01H 6/10* (2018.05)

(58) Field of Classification Search
USPC ..... Plt./490
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Zantedeschia* plant named 'EYD21WC102', characterized by its upright and broadly arching plant habit; high production of cut flowering stems; large white-colored spathes with strong and erect scapes; good cut flower postproduction longevity; and relative tolerance to Soft Rot (*Erwinia carotovora*) and aphids.

3 Drawing Sheets

Figure 1:
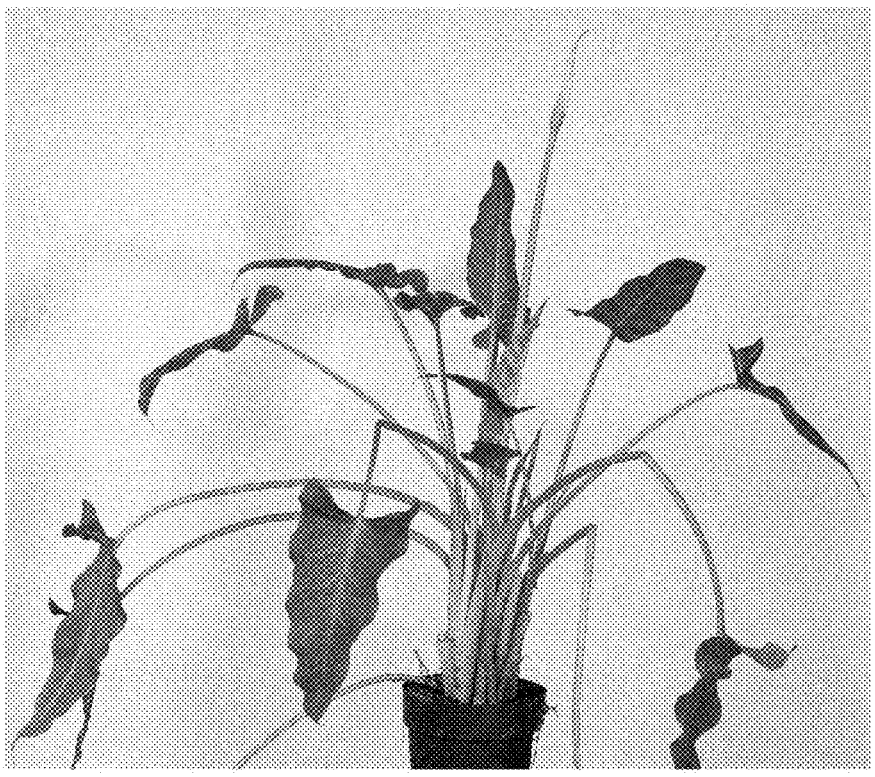

Botanical designation: *Zantedeschia aethiopica.*
Cultivar denomination: 'EYD21WC102'.

PREVIOUSLY-FILED INTERNATIONAL APPLICATIONS

A European Community Plant Breeder's Rights application for the instant plant was filed by the Applicant/Assignee of the instant application, Eijco B. V. of Nootdorp, The Netherlands on Nov. 27, 2023, application number 2023/2528 and published on Feb. 15, 2024. Foreign priority is not claimed to this application.

A United Kingdom Plant Breeder's Rights application for the instant plant was filed by Mr. Paul Gooderham, the United Kingdom's Agent of the Applicant/Assignee, of the instant application, Eijco B. V. of Nootdorp, The Netherlands on Oct. 7, 2024, application number 616/6 and published on Nov. 1, 2024. Foreign priority is not claimed to this application.

BACKGROUND OF THE INVENTION

The present invention relates to a new and distinct cultivar of *Zantedeschia* plant, typically grown as a cut flower, botanically known as *Zantedeschia aethiopica*, commonly referred to as Calla Lily and hereinafter referred to by the name 'EYD21WC102'.

The new *Zantedeschia* plant is a product of a controlled breeding program conducted by the Inventor in Nootdorp, The Netherlands. The objective of the breeding program is to create new freely flowering *Zantedeschia* plants that have large inflorescences and good postproduction longevity.

The new *Zantedeschia* plant originated from a cross-pollination in June 2015, in Nootdorp, The Netherlands of an unidentified proprietary selection of *Zantedeschia aethiopica*, not patented, as the female, or seed, parent with an unidentified proprietary selection of *Zantedeschia aethiopica*, not patented, as the male, or pollen, parent. The new *Zantedeschia* was discovered and selected by the Inventor as a single flowering plant within the progeny of the stated cross-pollination in a controlled greenhouse environment in Nootdorp, The Netherlands in May 2017.

Asexual reproduction of the new *Zantedeschia* plant by rhizomes and rhizome division in a controlled environment in Quelfes, Portugal since July 2020 has shown that the unique features of this new *Zantedeschia* plant are stable and reproduced true to type in successive generations of asexual reproduction.

SUMMARY OF THE INVENTION

Plants of the new *Zantedeschia* have not been observed under all possible combinations of environmental and cultural conditions. The phenotype may vary somewhat with variations in environment such as temperature and light intensity, without, however, any variance in genotype.

The following traits have been repeatedly observed and are determined to be the unique characteristics of 'EYD21WC102'. These characteristics in combination distinguish 'EYD21WC102' as a new and distinct cultivar of *Zantedeschia:*

1. Upright and broadly arching plant habit.
2. High production of cut flowering stems.
3. Large white-colored spathes with strong and erect scapes.
4. Good cut flower postproduction longevity.
5. Relatively tolerant to Soft Rot (*Erwinia carotovora*) and aphids.

Plants of the new *Zantedeschia* can be compared to the parent selections. Plants of the new *Zantedeschia* differ from plants of the female parent selection in plant habit as plants of the new *Zantedeschia* are more uniform than plants of the parent selections. In addition, plants of new *Zantedeschia* produce more flowering stems than plants of the parent selections.

Plants of the new *Zantedeschia* can also be compared to plants of *Zantedeschia aethiopica* 'Flamingo', disclosed in U.S. Plant Pat. No. 21,134. In side-by-side comparisons, plants of the new *Zantedeschia* differ from plants of 'Flamingo' in the following characteristics:

1. Plants of the new *Zantedeschia* are shorter than plants of 'Flamingo'.
2. Plants of the new *Zantedeschia* produce more flowering stems per meter than plants of 'Flamingo'.
3. Plants of the new *Zantedeschia* have white-colored flowers whereas plants of 'Flamingo' have pink-colored flowers.
4. Plants of the new *Zantedeschia* are more tolerant to root pathogens common to *Zantedeschia* plants than plants of 'Flamingo'.

BRIEF DESCRIPTION OF THE PHOTOGRAPHS

The accompanying photographs illustrate the overall appearance of the new *Zantedeschia* plant. These photographs show the colors as true as it is reasonably possible to obtain in colored reproductions of this type. Colors in the photographs may differ slightly from the color values cited in the detailed botanical description which accurately describe the colors of the new *Zantedeschia*.

The photograph on the first sheet (FIG. 1) is a side perspective view of a typical plant of 'EYD21WC102' grown in a container.

Figure 2:
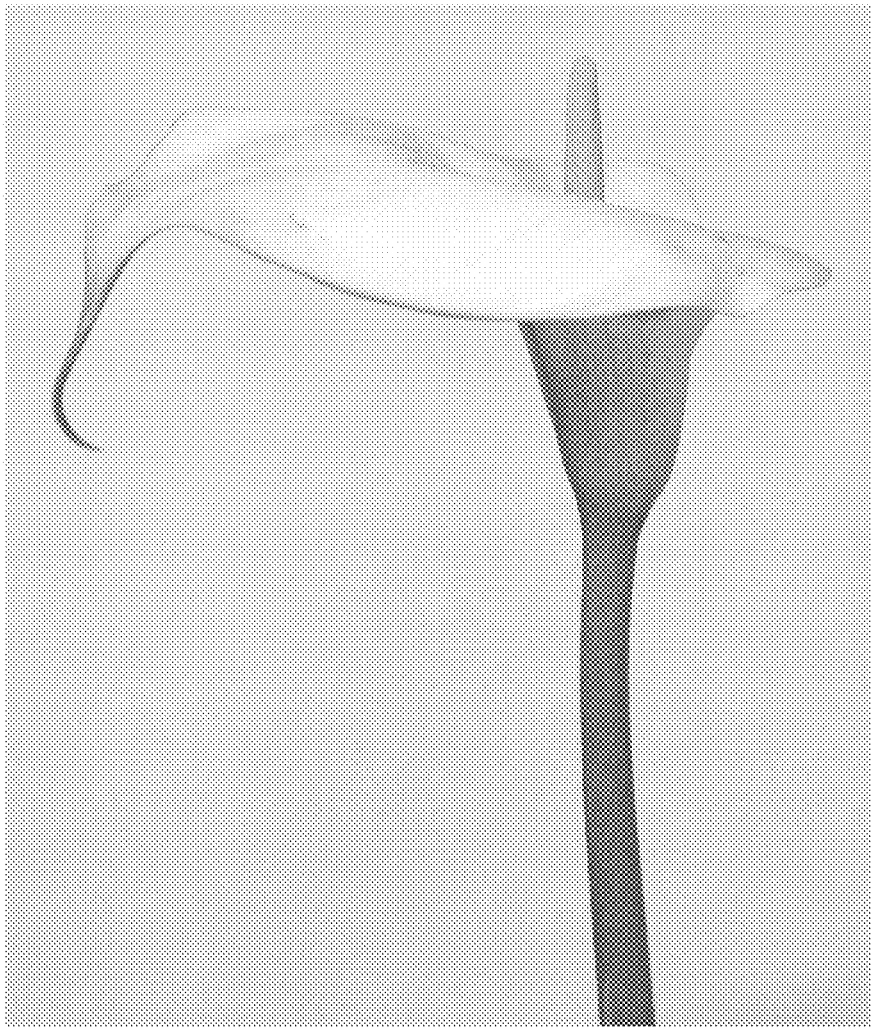

The photograph on the second sheet (FIG. 2) is a close-up view of a typical inflorescence of 'EYD21WC102'.

Figure 3:
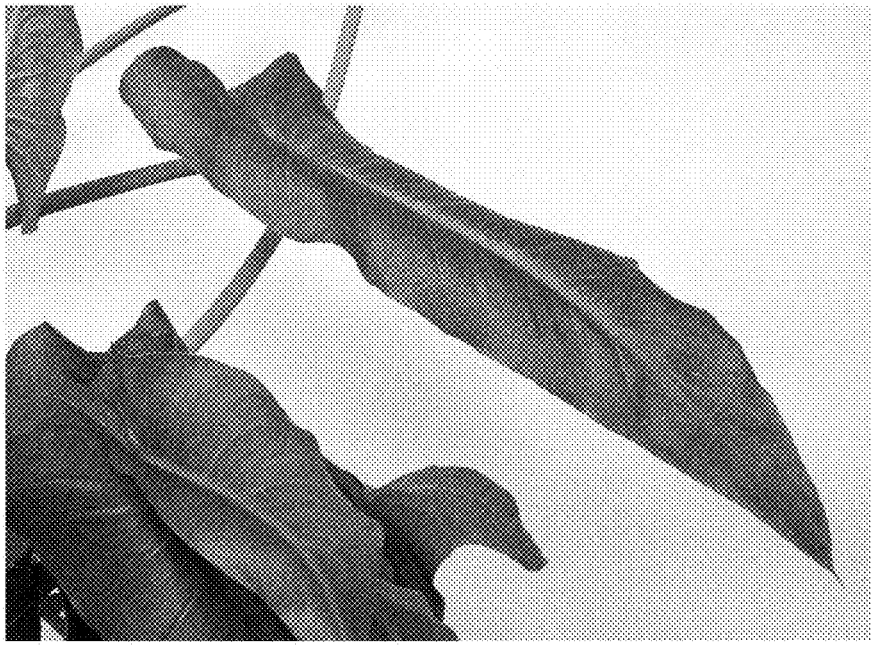

The photograph on the third sheet (FIG. 3) is a close-up view of typical leaves of 'EYD21WC102'.

DETAILED BOTANICAL DESCRIPTION

The aforementioned photographs and following observations and measurements describe plants grown during the spring in 17-cm containers in a glass-covered greenhouse in Pijnacker, The Netherlands. Plants were grown under conditions and practices which approximate those generally used in commercial *Zantedeschia* cut flower production. During the production of the plants, day temperatures ranged from 15° C. to 25° C. and night temperatures ranged from 5° C. to 15° C. Plants were 50 weeks old when the photographs were taken and two years old when the detailed description was taken. In the following description, color references are made to The Royal Horticultural Society Colour Chart, Sixth Edition, 2019 Reprint, except where general terms of ordinary dictionary significance are used.

Botanical classification: *Zantedeschia aethiopica* 'EYD21WC102'.

Parentage:

*Female, or seed, parent*.—Unidentified proprietary selection of *Zantedeschia aethiopica*, not patented.

*Male, or pollen, parent*.—Unidentified proprietary selection of *Zantedeschia aethiopica*, not patented.

Propagation:

*Type*.—By rhizomes or by rhizome division.

*Time to initiate roots*.—Variable, typically about one week at temperatures about 12° C. to 15° C.

*Time to produce a rooted young plant*.—Variable, typically about two months at temperatures about 12° C. to 19° C.

*Root description*.—Medium in thickness, fleshy; typically white in color; actual color of the roots is dependent on substrate composition, water quality, fertilizer, substrate temperature and age of roots.

*Rooting habit*.—Moderately freely branching; medium density.

Plant description:

*Plant habit*.—Upright and broadly arching plant habit; in outline, broad inverted triangle.

*Growth habit*.—Basally clumping; moderately vigorous to vigorous growth habit and moderate growth rate; about seven flowering stems develop per plant.

*Plant height, from soil level to top of leaf plane*.—About 74.3 cm.

*Plant height, from soil level to top of inflorescences*.—About 75 cm.

*Plant diameter or spread*.—About 87.7 cm.

*Leaf description*.—Arrangement: Alternate, basal; simple. Length: About 26.8 cm. Width: About 12.9 cm. Shape: Sagittate. Apex: Narrowly acute with mucronate tip. Base: Sagittate. Margin: Entire; moderately to strongly and coarsely undulate. Texture and luster, upper and lower surfaces: Smooth, glabrous; slightly leathery; moderately glossy. Venation pattern: Pinnate. Color: Developing leaves, upper and lower surfaces: Close to 144A. Fully expanded leaves, upper surface: Close to 143A; venation, close to 144A. Fully expanded leaves, lower surface: Close to a blend of 143B and 144A; venation, close to N144C and N144D. Petioles: Length: About 58.2 cm. Diameter, distally: About 7 mm. Diameter, proximally: About 1.25 cm by 1.5 cm. Texture and luster, upper and lower surfaces: Smooth, glabrous; slightly glossy. Color, upper surface: Close to 144A. Color, lower surface: Close to a blend of 144A and 144B. Wing length: About 26.3 cm. Wing diameter: About 6 mm. Wing color: Close to 145D; venation, close to 144C.

Inflorescence description:

*Inflorescence arrangement*.—Spathes with spadices positioned within to slightly above the foliar plane on strong and erect scapes; spathes, cup-shaped and revolute; spadices, cylindrical and tapering towards the apex.

*Inflorescence diameter*.—About 5.4 cm by 7.8 cm.

*Inflorescence depth*.—About 6.7 cm.

*Fragrance*.—Faintly fragrant; sweet and pleasant.

*Flowering season*.—In The Netherlands, flowering is continuous from spring into autumn; plants begin flowering about four to five months after planting rooted young plants.

*Quantity of inflorescences per plant*.—During the flowering season, typically about four inflorescences develop per plant.

*Inflorescence longevity*.—Depending on temperatures, inflorescences last about two weeks; inflorescences persistent.

*Spathe*.—Length: About 11.9 cm. Width: About 7.8 cm. Shape: Broadly cordate; cup-shaped. Apex: Broadly acute with an elongated mucronate tip. Base: Cordate; lobes slightly imbricate. Margin: Entire; revolute; slightly and coarsely undulate. Texture and luster, upper and lower surfaces: Smooth, glabrous; matte. Aspect: About 80° to 100° from peduncle axis. Color: When developing, upper surface: Close to 157A fading towards the base to close to a blend of 145D and 150D; towards the apex and at the apex, close to 144B. When developing, lower surface: Close to 150D fading towards the base to close to 150A; towards the apex and at the apex, close to 144B; midvein, close to 150B and 150C. Fully developed, upper surface: Close to 157D fading towards the base to close to 157B and 157C; towards the apex and at the apex, close to 144B. Fully developed, lower surface: Close to 155C fading towards the base to close to 150B; towards the apex and at the apex, close to 144B.

*Spadix*.—Length: About 5 cm. Diameter: About 8 mm. Shape: Cylindrical, tapering towards the apex; apex, obtuse; base, obtuse; cross-section, rounded. Aspect: About 15° from the peduncle axis. Color: Immature: Close to 10A and 11A. Mature: Close to 17A. Flowers, female: Arrangement and quantity: Positioned on the lower 20% of the spadix; about 50 per spadix. Shape: Rounded, flat. Height: About 1 mm. Diameter: About 1 mm. Stigma color: Close to 164B. Ovary color: Close to 194D. Flowers, male: Arrangement and quantity: Positioned on the upper 80% of the spadix; about 1,200 per spadix. Shape: Rounded, flat. Height: About 0.5 mm. Diameter: About 1 mm. Anther color: Close to 17A. Pollen amount: Abundant. Pollen color: Close to NN155A.

*Scape*.—Length: About 59.3 cm. Diameter, proximally: About 1 cm. Diameter, distally: About 6 mm. Strength: Strong. Aspect: Erect to about 20° from vertical. Color, proximally: Close to 147D; venation, close to 144C. Color, distally: Close to 144B; venation, close to 144C.

*Seed and fruit*.—To date, seed and fruit development has not been observed on plants of the new *Zantedeschia*.

Pathogen and pest tolerance: Plants of the new *Zantedeschia* have been observed to be relatively tolerant to Soft Rot (*Erwinia carotovora*) and aphids. Plants of the new *Zantedeschia* have not been observed to be tolerant to other pathogens and pests common to *Zantedeschia* plants.

Temperature tolerance: Plants of the new *Zantedeschia* are suitable for USDA Hardiness Zones 9 through 12.

It is claimed:

1. A new and distinct *Zantedeschia* plant named 'EYD21WC102' as herein illustrated and described.

* * * * *